US009642559B2

United States Patent
Falconio-West et al.

(10) Patent No.: US 9,642,559 B2
(45) Date of Patent: May 9, 2017

(54) COMPRESSION DEVICE WITH SIZING INDICIA

(71) Applicant: Medline Industries, Inc., Mundelein, IL (US)

(72) Inventors: Margaret Falconio-West, Round Lake, IL (US); Kristy Matus, Libertyville, IL (US); Jack Bowser, Round Lake, IL (US)

(73) Assignee: Medline Industries, Inc., Northfield, IL (US)

( * ) Notice: Subject to any disclaimer, the term of this patent is extended or adjusted under 35 U.S.C. 154(b) by 1145 days.

(21) Appl. No.: 13/649,920

(22) Filed: Oct. 11, 2012

(65) Prior Publication Data

US 2014/0107546 A1    Apr. 17, 2014

(51) Int. Cl.
*A61B 5/107* (2006.01)
*A61H 9/00* (2006.01)
(Continued)

(52) U.S. Cl.
CPC .......... *A61B 5/1072* (2013.01); *A61B 5/6812* (2013.01); *A61B 5/6824* (2013.01); *A61B 5/6828* (2013.01); *A61B 5/6831* (2013.01); *A61F 13/08* (2013.01); *A61B 5/0295* (2013.01); *A61H 9/005* (2013.01); *A61H 9/0078* (2013.01)

(58) Field of Classification Search
CPC ... A61B 5/1072; A61B 5/6828; A61B 5/6824; A61B 5/6812; A61B 5/0295; A61H 9/005; A61H 9/0078; A61F 13/08
See application file for complete search history.

(56) References Cited

U.S. PATENT DOCUMENTS 3,011,494 A   12/1961   McGowan
1,562,454 A   11/1965   Jankins
(Continued)

FOREIGN PATENT DOCUMENTS

WO    WO-94/01071    1/1994

OTHER PUBLICATIONS

"DeRoyal Medical Products PRUventor", "*PRUventor Heel Off-loading Device*"; Publication Date Unknown but believed to be before the filing date of the present application; http://www.deroyal.com/MedicalProducts/.

(Continued)

*Primary Examiner* — Justine Yu
*Assistant Examiner* — Timothy Stanis
(74) *Attorney, Agent, or Firm* — Philip H. Burrus, IV

(57) ABSTRACT

A compression device (100) configured to provide compression therapy is provided. The compression device includes a wrap (101) having an outer face (105) defining a proximal edge (106), a distal edge (107), a first side edge (108), and a second side edge (109). The second side edge may include a plurality of attachment tabs (110,111,112). An index line (113) can be disposed on at least one of the plurality of attachment tabs. A measurement scale (114) can be disposed along the outer face. The measurement scale can include longitudinal boundaries (115,116) identifying a range within which the index line should position for the compression device to provide an appropriate fit for compression therapy when the compression device is wrapped about a patient's limb.

20 Claims, 9 Drawing Sheets

(51) Int. Cl.
*A61F 13/08* (2006.01)
*A61B 5/00* (2006.01)
*A61B 5/0295* (2006.01)

(56) References Cited

U.S. PATENT DOCUMENTS

| | | | |
|---|---|---|---|
| 3,216,417 A | 11/1965 | Posey | |
| 3,279,459 A | 10/1966 | Schenker | |
| 3,490,450 A | 1/1970 | Gardner | |
| 3,674,023 A | 7/1972 | Mann | |
| 3,693,619 A | 9/1972 | Williams | |
| D225,472 S | 12/1972 | Lowrey et al. | |
| 3,721,237 A | 3/1973 | Alessio | |
| 3,905,135 A | 9/1975 | Debusk | |
| D239,058 S | 3/1976 | Gaylord, Jr. | |
| 3,955,565 A | 5/1976 | Johnson, Jr. | |
| 4,135,504 A | 1/1979 | Spann | |
| 4,186,738 A | 2/1980 | Schleicher et al. | |
| 4,266,298 A | 5/1981 | Graziano | |
| D261,821 S | 11/1981 | Hubbard et al. | |
| D268,365 S | 3/1983 | Malkin | |
| 4,441,493 A | 4/1984 | Nirschl | |
| 4,573,482 A | 3/1986 | Williams, Jr. | |
| 4,597,395 A | 7/1986 | Barlow et al. | |
| 4,624,244 A | 11/1986 | Taheri | |
| 4,730,610 A | 3/1988 | Graebe | |
| RE32,680 E | 5/1988 | Pompa | |
| 4,781,133 A | 11/1988 | Hanyu et al. | |
| 4,947,834 A | 8/1990 | Kartheus et al. | |
| 4,972,832 A * | 11/1990 | Trapini | A61F 7/02 602/2 |
| 5,052,128 A | 10/1991 | Lonardo | |
| 5,226,245 A | 7/1993 | Lamont | |
| D338,067 S | 8/1993 | Luber et al. | |
| D343,002 S | 1/1994 | Gauvry | |
| 5,288,286 A | 2/1994 | Davis et al. | |
| D352,381 S | 11/1994 | Rose | |
| 5,367,789 A | 11/1994 | Lamont | |
| 5,435,009 A | 7/1995 | Schild et al. | |
| 5,449,339 A | 9/1995 | Drennan | |
| 5,464,385 A | 11/1995 | Grim | |
| 5,479,471 A | 12/1995 | Buckland | |
| 5,511,552 A | 4/1996 | Johnson | |
| 5,588,954 A | 12/1996 | Ribando | |
| 5,626,556 A | 5/1997 | Tobler et al. | |
| 5,649,954 A * | 7/1997 | McEwen | A61B 17/135 600/490 |
| 5,660,182 A | 8/1997 | Kuroshaki et al. | |
| 5,827,211 A | 10/1998 | Sellinger | |
| 5,833,639 A | 11/1998 | Nunes et al. | |
| 5,868,690 A | 2/1999 | Eischen, Sr. | |
| D410,746 S | 6/1999 | Klein | |
| 6,080,120 A | 6/2000 | Sandman et al. | |
| 6,126,627 A | 10/2000 | Brennan | |
| 6,152,893 A | 11/2000 | Pigg et al. | |
| 6,277,087 B1 | 8/2001 | Hess et al. | |
| 6,308,713 B1 | 10/2001 | Coleman | |
| 6,322,530 B1 | 11/2001 | Johnson, Jr. et al. | |
| 6,338,723 B1 | 1/2002 | Carpenter et al. | |
| D453,969 S | 2/2002 | Callsen et al. | |
| D455,836 S | 4/2002 | Lammers | |
| 6,572,573 B1 | 6/2003 | Klein | |
| 6,640,810 B1 | 11/2003 | Callsen et al. | |
| 7,004,920 B2 | 2/2006 | Fareed | |
| D517,306 S | 3/2006 | Hoeft | |
| 7,052,479 B2 | 5/2006 | Drennan | |
| 7,115,105 B2 | 10/2006 | Cropper | |
| D542,921 S | 5/2007 | Ponsi et al. | |
| D544,101 S | 6/2007 | Kistner | |
| 7,252,647 B1 | 8/2007 | Hely | |
| D551,354 S | 9/2007 | McBarnett et al. | |
| 7,276,037 B2 | 10/2007 | Ravikumar | |
| 7,329,232 B2 | 2/2008 | Lipshaw et al. | |
| D571,083 S | 6/2008 | Mohammad | |
| 7,455,651 B2 | 11/2008 | Mollica | |
| 7,458,948 B2 | 12/2008 | Drennan | |
| 7,798,984 B2 | 9/2010 | Ponsi et al. | |
| 8,152,749 B2 | 4/2012 | Ponsi et al. | |
| 8,216,165 B2 | 7/2012 | Ravikumar et al. | |
| 8,241,263 B2 | 8/2012 | Mills | |
| 8,251,932 B2 | 8/2012 | Fout | |
| 8,435,199 B2 | 5/2013 | Ponsi et al. | |
| D697,628 S | 1/2014 | Drey et al. | |
| D731,158 S | 6/2015 | Backus | |
| D749,744 S | 2/2016 | Drey | |
| 2001/0051240 A1* | 12/2001 | Denis | A01G 13/0225 428/36.1 |
| 2003/0168063 A1* | 9/2003 | Gambone | A61M 16/06 128/203.16 |
| 2004/0111048 A1 | 6/2004 | Jensen et al. | |
| 2004/0236261 A1 | 11/2004 | McCarthy | |
| 2005/0131321 A1 | 6/2005 | Ravikumar | |
| 2005/0171461 A1 | 8/2005 | Pick | |
| 2005/0192524 A1* | 9/2005 | Lipshaw | A61F 13/06 602/62 |
| 2007/0032773 A1 | 2/2007 | Magee | |
| 2007/0074427 A1 | 4/2007 | Ponsi et al. | |
| 2008/0022559 A1 | 1/2008 | Ponsi | |
| 2009/0076427 A1 | 3/2009 | Ponsi | |
| 2009/0149791 A1 | 6/2009 | Ponsi et al. | |
| 2009/0227927 A1 | 9/2009 | Frazer | |
| 2010/0082060 A1* | 4/2010 | Avitable | A61H 9/0078 606/202 |
| 2010/0152638 A1 | 6/2010 | Ponsi et al. | |
| 2010/0312160 A1 | 12/2010 | Creighton et al. | |
| 2010/0324517 A1* | 12/2010 | Lenhult | A61F 13/5622 604/385.01 |
| 2011/0125183 A1 | 5/2011 | Lipshaw et al. | |
| 2011/0180074 A1 | 7/2011 | Gainey | |
| 2012/0012118 A1 | 1/2012 | Ponsi et al. | |
| 2012/0179082 A1 | 7/2012 | Ponsi et al. | |
| 2012/0193957 A1 | 8/2012 | Grover | |
| 2012/0209158 A1 | 8/2012 | Avitable et al. | |
| 2013/0085427 A1* | 4/2013 | Malhi | A61H 9/0092 601/148 |
| 2013/0085432 A1* | 4/2013 | Malhi | A61H 9/0078 601/151 |
| 2014/0107547 A1 | 4/2014 | Drey et al. | |
| 2014/0173940 A1 | 6/2014 | Drennan | |
| 2014/0194796 A1 | 7/2014 | Noskowicz et al. | |

OTHER PUBLICATIONS

Krakower, Susan "Notice of Allowance", U.S. Appl. No. 29/444,693, filed Feb. 1, 2013; Mailed Aug. 27, 2013.
Krakower, Susan "NonFinal OA", U.S. Appl. No. 29/473,963, filed Nov. 27, 2013; Mailed Jan. 24, 2014.
Han, Inho "PCT Search Report and Written Opinion", PCT/US2013/063852; Filed Oct. 8, 2013; Mailed Jan. 8, 2014.
Shin, Ju C., "PCT Search Report and Written Opinion", PCT/US2014/013780; File Jan. 30, 2014; Mailed May 19, 2014.
Krakower, Susan "Final OA", U.S. Appl. No. 29/473,963, filed Nov. 27, 2013; Mailed Jul. 7, 2014.
Han, Inho "PCT Search Report and Written Opinion", PCT/US2014/026259; Filed Mar. 13, 2014; Mailed Jul. 7, 2014.
"Flowtron Universal", *Arjo Huntleigh Publication; Flowtron Universal Publication*; Published 2009; pp. 1-4.
"Calibrated V-Lok Cuff", *Calibrated V-Lok Cuff Specification Publication*; Publicly available more than one year prior to the filing date of the present application.; Printed Sep. 2012; p. 1.
"Website", *Covidien Vascular Compression Products*; www.covidien.com/vascularcompression/pages.aspx; Publicly available prior to filing of this application.
Kroakower, Susan "Ex Parte Quayle", U.S. Appl. No. 29/473,963, filed Nov. 27, 2013; mailed Feb. 20, 2015.
"Medline Catalog", *EHOB Foot Waffle Heel Elevator by Ahmed; Medline Catalog*; http://www.medline.com/catalog/catalog.jsp; Unknown Publication date but believed to be prior to present application filing date.

(56) References Cited

OTHER PUBLICATIONS

"Medline Catalog", *Foot Waffle Air Cushion by Patterson Med; Medline Catalog*; http://www.medline.com/catalog/catalog.jsp; Unknown Publication date but believed to be prior to present application filing date.
"Medline Catalog", *Foot Waffle Custom by EHOB; Medline Catalog*; http://www.medline.com/catalog/catalog.jsp; Unknown Publication date but believed to be prior to present application filing date.
"Medline Catalog", *Foot Waffle Heel Elevator Custom by EHOB; Medline Catalog*; http://www.medline.com/catalog/catalog.jsp; Unknown Publication date but believed to be prior to present application filing date.
"Medline Catalog", *Prevalon Heel Protectors by Sage Products; Medline Catalog*; http://www.medline.com/catalog/catalog.jsp; Unknown Publication date but believed to be prior to present application filing date.
"Medline Catalog", *Waffle FootHold Splint with Anti-Rotation; Medline Catalog*; http://www.medline.com/catalog/catalog.jsp; Unknown Publication date but believed to be prior to present application filing date.
"Medline Catalog", Waffle FootHold with Secure stick Sole by EHOB; Medline Catalog; http://www.medline.com/catalog/catalog.jsp; Unknown Publication date but believed to be prior to present application filing date.
"Medline Catalog", *Waffle FootHold with Splint by EHOB; Medline Catalog*; http://www.medline.com/catalog/catalog.jsp; Unknown Publication date but believed to be prior to present application filing date.
"Medline Catalog", *Waffle Heel Elevator by EHOB; Medline Catalog*; http://www.medline.com/catalog/catalog.jsp; Unknown Publication date but believed to be prior to present application filing date.
"Medline Catalog", *Waffle Heel Protectors by EHOB; Medline Catalog*; http://www.medline.com/catalog/catalog.jsp; Unknown Publication date but believed to be prior to present application filing date.
Stanis, Timothy "NonFinal OA", U.S. Appl. No. 13/757,233, filed Feb. 1, 2013; Mailed Oct. 2, 2015.
Krawkower, Susan "Notice of Allowance", U.S. Appl. No. 29/473,963, filed Nov. 27, 2013; Mailed Oct. 20, 2015.
Stanis, Timothy "Final OA", U.S. Appl. No. 13/757,233, filed Feb. 1, 2013; Mailed Apr. 18, 2016.
Watkins, Jennifer "NonFinal OA", U.S. Appl. No. 29/500,542, filed Aug. 26, 2014; Mailed Mar. 8, 2016.
Stanis, Timothy "NonFinal OA", U.S. Appl. No. 14/206,395, filed Mar. 12, 2014; Mailed May 16, 2016.
Stanis, Timothy "Notice of Allowance", U.S. Appl. No. 13/757,233, filed Feb. 1, 2013; Mailed Jun. 22, 2016.
Watkins, Jennifer "Final OA", U.S. Appl. No. 29/500,542, filed Aug. 26, 2014; Mailed Jun. 28, 2016.
Watkins, Jennifer "Notice of Allowance", U.S. Appl. No. 29/500,542, filed Aug. 26, 2014; Mailed Nov. 2, 2016.
Stanis, Timothy "Final OA", U.S. Appl. No. 14/206,395, filed Mar. 12, 2014; Mailed Nov. 21, 2016.
"Medline Catalog", *BioCompression Pneumatic Sleeves by Ahmed; Medline Catalog*; http://www.medline.com/catalog/catalog.jsp; Unknown Publication date but believed to be prior to present application filing date.
"Medline Catalog", *Comfort Lined Sleeve by Ecolab/Microtek; Medline Catalog*; http://www.medline.com/catalog/catalog.jsp; Unknown Publication date but believed to be prior to present application filing date.
"Medline Catalog", *Flowtron Compression Garments by Gentinge; Medline Catalog*; http://www.medline.com/catalog/catalog.jsp; Unknown Publication date but believed to be prior to present application filing date.
"Medline Catalog", *Kendall SCD Compression System by Medtronic; Medline Catalog*; http://www.medline.com/catalog/catalog.jsp; Unknown Publication date but believed to be prior to present application filing date.
"Medline Catalog", *Leg Compression Garments by Currie Medical; Medline Catalog*; http://www.medline.com/catalog/catalog.jsp; Unknown Publication date but believed to be prior to present application filing date.
"Medline Catalog", *Rolyan Neoprene Elbow Sleeve by Patters; Medline Catalog*; http://www.medline.com/catalog/catalog.jsp; Unknown Publication date but believed to be prior to present application filing date.
"Medline Catalog", *SCD Express Compression System by Covidien; Medline Catalog*; http://www.medline.com/catalog/catalog.jsp; Unknown Publication date but believed to be prior to present application filing date.
"Medline Catalog", *SCD Express Sleeve (Knee Length) by Stryker; Medline Catalog*; http://www.medline.com/catalog/catalog.jsp; Unknown Publication date but believed to be prior to present application filing date.
"Medline Catalog", *SCD Express Thigh Length Sleeves by Covidien; Medline Catalog*; http://www.medline.com/catalog/catalog.jsp; Unknown Publication date but believed to be prior to present application filing date.
"Medline Catalog", *VasoGrad Dvt Sleeves by Compression Therapy Concepts; Medline Catalog*; http://www.medline.com/catalog/catalog.jsp; Unknown Publication date but believed to be prior to present application filing date.

* cited by examiner

COMPRESSION DEVICE WITH SIZING INDICIA

BACKGROUND

Technical Field

This invention relates generally to compression devices, and more particularly to compression devices for providing compression therapy to a patient.

Background Art

Compression devices are used to apply compressive pressure to a patient's limb. These devices are generally configured in the form of a garment that can be wrapped about the limb. They can include an inflatable bladder that is inflated to increase the amount of pressure being applied to the limb. The pressure applied can cause blood flow velocity to increase, thereby providing a therapeutic effect.

Compression devices are used to provide therapy in a variety of applications. Illustrating by example, compression devices can be used to prevent deep vein thrombosis (DVT), which is a condition where clots form in the blood. Patients undergoing surgery, under anesthesia, or undergoing extended periods of bed rest are at risk of clotting conditions associated with DVT. The clotting conditions frequently occur in the deep veins of the lower extremities, such as in the lower legs, due to the tendency of blood to accumulate or pool in these areas. Static pools of blood can give rise to clotting conditions. Where clots form, circulation can be compromised, thereby putting the patient's health at risk. Further, clots can break free, which puts the patient at risk for embolism, which in some circumstances can be life threatening. Application of a compression device can work to prevent pooling, thereby reducing the risk that a clot will form.

A problem associated with prior art compression devices is that they can lead to skin breakdown or pressure ulcers due to improper fit. Such problems can arise whether the compression device is too large or too small. Ideally, a health care services provider should measure the patient's limb to determine what size compression device to use, and then order an appropriately sized device. However, this rarely happens. Frequently, a health care services provider will simply try to twist, fold, or otherwise manipulate an ill-fitting compression device to get it to wrap about the patient's limb. This manipulation increases the risk of skin breakdown or pressure ulcers. Additionally, if the compression device is too large, it can slide up and down on the patient's leg, which leads to the formation of undesirable pressure points. Proper compression generally cannot be achieved with an ill-fitting compression device either. The manipulation of an ill-fitting compression device is not only uncomfortable for the patient, but costly as well due to the fact that untreated ulcers can lead to conditions such as osteomyelitis and even the necessitation of amputating the limb.

It would be advantageous to have an improved compression device.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
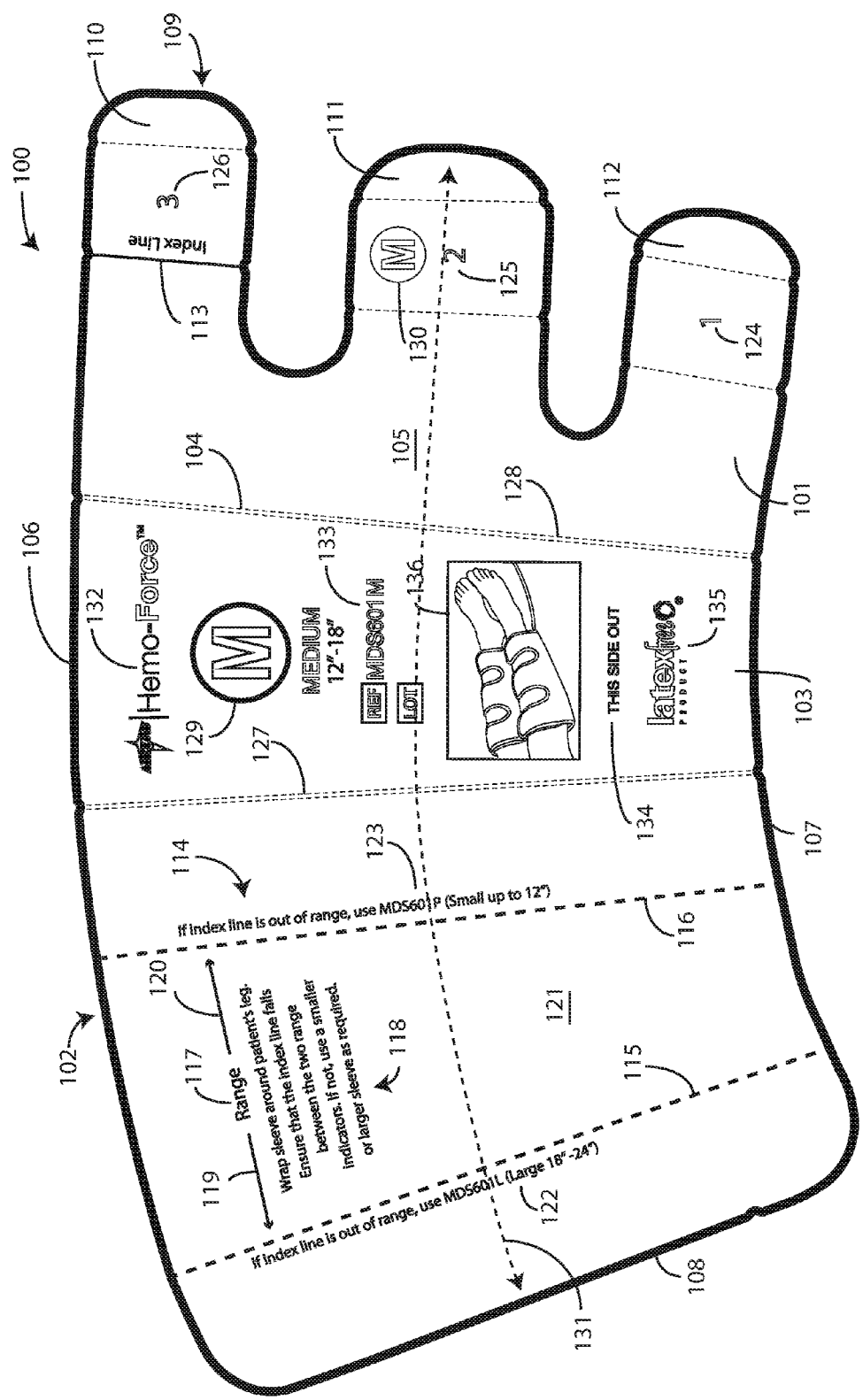
FIG. 1 illustrates a top plan view of one explanatory compression device configured for providing compression therapy to a patient limb in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. The term "proximal" as used herein refers to a portion of a structure that is closer to a torso of a patient. Similarly, the term "distal" refers to a portion that is further from the torso. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a compression device configured for providing compression therapy to a patient's limb. In one embodiment, the compression device comprises a wrap material, which can be elasticized, that has an outer face and an inner face. The inner face is disposed against the patient's limb, while the outer face is visible when the wrap is applied to the limb. The wrap defines a proximal edge, a distal edge, and first and second side edges. One of the side edges includes a plurality of attachment tabs that are configured to attach—by hook and loop fastener or other attachment device—to the outer face when the wrap is wrapped about the patient's limb.

To ensure that a health care services provider applies a properly sized compression device, in one embodiment one of the attachment tabs includes an index line. The outer face includes a measurement scale disposed thereon. The measurement scale includes, in one embodiment, longitudinal boundaries identifying a range within which the index line should position for the compression device to provide an appropriate fit for the provision of the compression therapy when the compression device is wrapped about the patient limb.

Where the selected compression device does not fit properly, the index line will not position within the longitudinal boundaries. However, to alert the health care services provider regarding what should be done in such a case, in one embodiment instructional indicia is included with the measurement gauge. For example, the measurement scale can include instructions, disposed between one of the longitudinal boundaries and one of the side edges that indicate a larger compression device is required. The health care services provider would be alerted to this instruction when the index line positions between the longitudinal boundary and the side edge after the compression device is wrapped about the patient limb. Similarly, additional instructions can be disposed on the other side of the measurement scale. In one embodiment, the additional instructions are disposed between another of the longitudinal boundaries and another side edge. When the index line falls outside the measurement scale on the side of the other longitudinal boundary, the instructions indicate that a smaller compression device is required.

In one embodiment, ordinal numbers are applied to each of the attachment tabs. The ordinal numbers indicate a sequence in which the attachment tabs should be attached to most effectively reduce the risk of conditions such as DVT. In some embodiments, the wrap can include a central panel having indicia identifying a size of the compression device disposed thereon. In some embodiments, one of the attachment tabs has corresponding indicia identifying the size of the compression device disposed thereon as well. Further, in some embodiments, any of the major face, a border, or combinations thereof can be color-coded with colors corresponding with the size as well.

A method of applying a compression device to a patient's limb is also disclosed. For example, in one embodiment, the method includes wrapping the compression device about the patient limb and attaching an attachment tab of the compression device to an outer face of the compression device. The method then includes determining whether an index line disposed on the attachment tab is within a measurement scale disposed on the outer face of the compression device. Where it is, the health care services provider is assured that they have selected an appropriately fitting compression device.

However, when the index line positions between a longitudinal boundary of the measurement scale and a first side edge of the compression device, the health care services provider is directed to instructions indicating that a larger compression device should be obtained. Similarly, when the index line positions between another longitudinal boundary of the measurement scale and a second side edge of the compression device, the health care services provider will be directed to additional instructions suggesting that a smaller compression device be obtained. Where the attachment tabs include ordinal numbers indicating the sequence in which they should be attached, the method includes determining the ordinal numbers and attaching each of the plurality of attachment tabs in an order corresponding to the ordinal numbers.

Turning now to FIG. 1, illustrated therein is a top, plan view of one explanatory compression device 100 configured for providing compression therapy to a patient limb's in accordance with one or more embodiments of the invention. The compression device can be configured to wrap about various limbs, including a leg, arm, or other body part. In one embodiment, the compression device 100 is configured to wrap about the leg of a patient. However, those of ordinary skill in the art having the benefit of this disclosure will appreciate that the compression device 100 could equally be configured as an arm cuff, a knee sleeve, or sleeve for another body part.

The compression device 100 comprises a wrap 101 configured to wrap about the patient's limb. In one embodiment, the wrap 101 is manufactured from a non-stretchable material. In other embodiments, the wrap 101 is manufactured from a stretchable, elasticized material. The wrap 101 can comprise one or more layers of material that are stitched together. For example, in one embodiment, the wrap 101 comprises at least two layers of material that are stitched together along a perimeter 102. Panels, e.g., central panel 103, can also be defined along the wrap 101 by stitching 104 as well. The stitching 104 can be replaced by other suitable means for joining the materials, such as high frequency welds, ultrasonic welding, thermal bonding, heat-sealing, or adhesive bonding.

One example of a suitable material for the wrap 101 is nylon tricot. Nylon tricot is manufactured by machines that use a warp-knit pattern to weave nylon fiber. The fibers are typically woven across the width of the material layer in a zigzag pattern. The nylon tricot can be 100% nylon fiber, or can alternatively be a blend of nylon and other fibers, including rayon or cotton. Nylon tricot works well as the wrap 101 because it does not snag or run easily. Moreover, it can be manufactured in a variety of colors. Nylon tricot can also be machine-washed.

Other materials can be used as the wrap 101 as well. For instance, the wrap 101 can be manufactured from one or more sheets of plastic, neoprene, rubber, foam, felt, polymers, resins, and/or natural fabric materials. In some embodiments, only some layers of the wrap 101 can be configured to be stretchy and elastic. For instance, the outer face 105 shown in FIG. 1 can be manufactured from a stretchy material, such as tricot stretch fabric, while an inner face is manufactured from a non-elastic material, or vice versa. Additionally, the various layers of the wrap 101 may be manufactured from materials having varying degrees of elasticity or stretchiness.

In the illustrative embodiment of FIG. 1, the wrap 101 and its outer face 105 define a proximal edge 106, a distal edge 107, a first side edge 108, and a second side edge 109. In this embodiment, the second side edge 109 defines a plurality of attachment tabs 110,111,112. In one embodiment, the outer face 105 of the wrap 101 and the attachment tabs 110,111, 112 work in tandem to allow the attachment tabs 110,111, 112 to attach to the outer face 105. In one embodiment the wrap 101 and attachment tabs 110,111,112 employ hook and loop fastening devices for attachment. For example, each of the attachment tabs 110,111,112 can include hook fasteners disposed on the inner face (disposed opposite the outer face 105 and not shown in FIG. 1), while the wrap 101 comprises loop pile fabric to which the hook fasteners can attach. Alternatively, loop fasteners can be disposed along the outer face 105 to provide an attaching surface. It will be obvious to those of ordinary skill in the art having the benefit of this disclosure that other attachment mechanisms can be used, such as zippers, buttons, straps, laces, adhesive, or other devices.

In one embodiment, one of the attachment tabs 110,111, 112 has an index line 113 disposed thereon. While the index line 113 can be disposed upon multiple attachment tabs 110,111,112, in the illustrative embodiment of FIG. 1, the index line 113 is disposed only on the attachment tab 110 located adjacent to the proximal edge 106 of the wrap 101.

To ensure that the appropriate fit is achieved when applying the compression device 100 to the patient's limb, in one embodiment the outer face 105 of the wrap 101 has a measurement scale 114 disposed thereon. In the illustrative embodiment of FIG. 1, the measurement scale 114 comprises two longitudinal boundaries 115,116 identifying a range within which the index line 113 should position for the compression device 100 to provide an appropriate fit for providing compression therapy when the compression device 100 is wrapped about the patient limb. Accordingly, when the wrap 101 is wrapped about the limb and attachment tab 110 is attached to the outer face 105, an appropriate fit is achieved when the index line 113 lands within the two longitudinal boundaries 115,116.

In the illustrative embodiment of FIG. 1, the longitudinal boundaries 115,116 are configured to fit a "medium" sized compression device 100. Illustrative dimensions for such longitudinal boundaries 115,116 can be as follows: longitudinal boundary 115 can be about four centimeters from the first side edge 108. Similarly, longitudinal boundary 116 can be about four centimeters from the stitching 127 of the central panel 103. Along the distal edge 107, the longitudinal boundaries 115,116 can be about ten centimeters apart. Along the proximal edge 106, the longitudinal boundaries 115,116 can be about eighteen centimeters. It should be noted that these dimensions are for one illustrative embodiment only, and are not to be considered limiting. Similar and/or proportional measurements may be used for other smaller and larger sizes, with the longitudinal boundaries 115,116 being predetermined distances from the edges of the wrap 101. Further, as will be shown below in FIG. 4, the longitudinal boundaries 115,116 need not extend all the way across the wrap 101. Other configurations of longitudinal boundaries 115,116 will be obvious to those of ordinary skill in the art having the benefit of this disclosure.

In the illustrative embodiment of FIG. 1, the measurement scale includes a range indicator 117 and usage instructions 118. This illustrative range indicator 117 comprises the word "range" and two arrows 119,120 that verify that the space 121 between the two longitudinal boundaries 115,116 is the proper landing area for the index line 113. The usage instructions 118 provide direction as to how to properly wrap the compression device 100 about the torso. For example, the illustrative usage instructions 118 of FIG. 1 state, "Wrap sleeve around patient's leg. Ensure that the index line falls between the two range indicators. If not, use a smaller or larger sleeve as required."

If the index line 113 does not land between the two longitudinal boundaries 115,116, in one or more embodiments the measurement scale 114 further comprises instructions 122,123 directing a health care services provider with specifics as to what action to take next. For example, a first set of instructions 122 is disposed between one of the longitudinal boundaries 115 and the first side edge 108. These instructions 122 indicate that a larger compression device is required. In the illustrative embodiment of FIG. 1, these instructions 122 also provide the part number that should be selected for convenience. The instructions 122 state, "If index line is out of range, use MDS601L (Large 18"-24")." A health care service provider's attention will be directed to these instructions 122 when the index line 113 positions between the longitudinal boundary 115 and the first side edge 108 when the compression device 100 is wrapped about the patient limb and attachment tab 110 is attached to the outer face 105.

Additional instructions 123 are provided when the compression device 100 is too large. Specifically, in the illustrative embodiment of FIG. 1, the additional instructions 123 are disposed between another of the longitudinal boundaries 116 and the second side edge 109. The additional instructions 123 indicate that a smaller compression device is required. As with instructions 122, the additional instructions 123 optionally provide a part number for user convenience. The additional instructions 123 state, "If index line is out of range, use MDS601P (Small up to 12")." A health care service provider's attention will be directed to these additional instructions 123 when the index line 113 positions between longitudinal boundary 116 and the second side edge 109 when the compression device 100 is wrapped about the patient limb and attachment tab 110 is attached to the outer face 105.

Other indicia can be disposed along the outer face 105 as well. For example, in the illustrative embodiment of FIG. 1, each of the attachment tabs 110,111,112 has an ordinal number 124,125,126 disposed thereon. In this embodiment, the ordinal numbers 124,215,126 indicate in which order the plurality of attachment tabs 110,111,112 are to be attached to the outer face 105 of the wrap 101. Experimental testing has shown that the most effective method for preventing DVT when applying the compression device 100 is to apply the most distal attachment tab 112 first, followed by the next attachment tab 111, and finally the most proximal attachment tab 110. This method helps to push blood back toward the patient's torso and works to prevent blood pooling distally from the compression device. Accordingly, attachment tab 110 has the lowest ordinal number 124, while the greatest ordinal number, i.e., ordinal number 126, is disposed on the attachment tab 110 located adjacent to the proximal edge 106 of the compression device 100.

In the illustrative embodiment of FIG. 1, the wrap 101 comprises a central panel 103 that is defined by two longitudinal stitches 127,128. To alert the health care services provider to the size of the compression device 100, the central panel also comprises indicia 129 identifying a size of the compression device 100, which in this case is a medium, defined by an inner diameter wrap length of between twelve and eighteen inches.

In one or more embodiments, to provide an additional mnemonic indicator of the size, at least one of the plurality of attachment tabs, in this case attachment tab 111, has corresponding indicia 130 identifying the size of the compression device 100 as well. As the index line 113 is disposed on attachment tab 110 in this embodiment, and the corresponding indicia 130 is disposed on attachment tab 111, the index line 113 and the corresponding indicia 130 identifying the size of the compression device 100 are disposed on different attachment tabs. However, it should be noted that they could be disposed on the same tab as well.

It is contemplated that other mnemonic indicators of size can be included as well. For example, in one embodiment, the outer face 105 is color-coded with a color visually indicative of the size. The wrap 101 can be manufactured in a particular color that corresponds to a particular size. In one embodiment, the wrap 101 is manufactured in yellow to represent a small size, grey to represent medium, red to represent large, and green to represent extra large.

In other embodiments, the wrap 101 can be manufactured from a common color, such as blue. However, piping disposed along the perimeter 102 can be color-coded with a color visually indicative of the size that is different from the color of the wrap 101. Accordingly, the combination of the color and the another color can be configured to be visually indicative of the size of the compression device 100. For example, while the outer face 105 is blue, the perimeter 102 can be color-coded such that it is yellow to represent a small size, grey to represent medium, red to represent large, and green to represent extra large.

As shown in FIG. 1, the first side edge 108 and the second side edge 109 are not parallel. This is due to the fact that a medial reference line 131 extending across the wrap 101 has a curvature configured to facilitate the wrap 101 wrapping around a patient's limb. This causes both the first side edge 108 and second side edge 109, and the longitudinal boundaries 115,116, respectively, to be oblique relative to each other so as to be substantially orthogonal with the imaginary medial reference line 131. Accordingly, the longitudinal boundaries 115,116 form a quasi-frustoconical shape ("quasi" because the top and bottom are curved in accordance with the curvature).

In one or more embodiments, additional graphical indicia can be disposed along the outer face 105 of the wrap as well. For example, in the illustrative embodiment of FIG. 1, a product name 132 and part number 133 are provided. Additionally, an indicator 134 of which side forms the outer face 105 is provided. Product specific information 135, such as information indicating that the product is latex free, can also optionally be provided. Diagrams and pictures 136 can be included to provide a quick reference for a health care services provider that visually depicts usage of the compression device 100.

Figure 2:
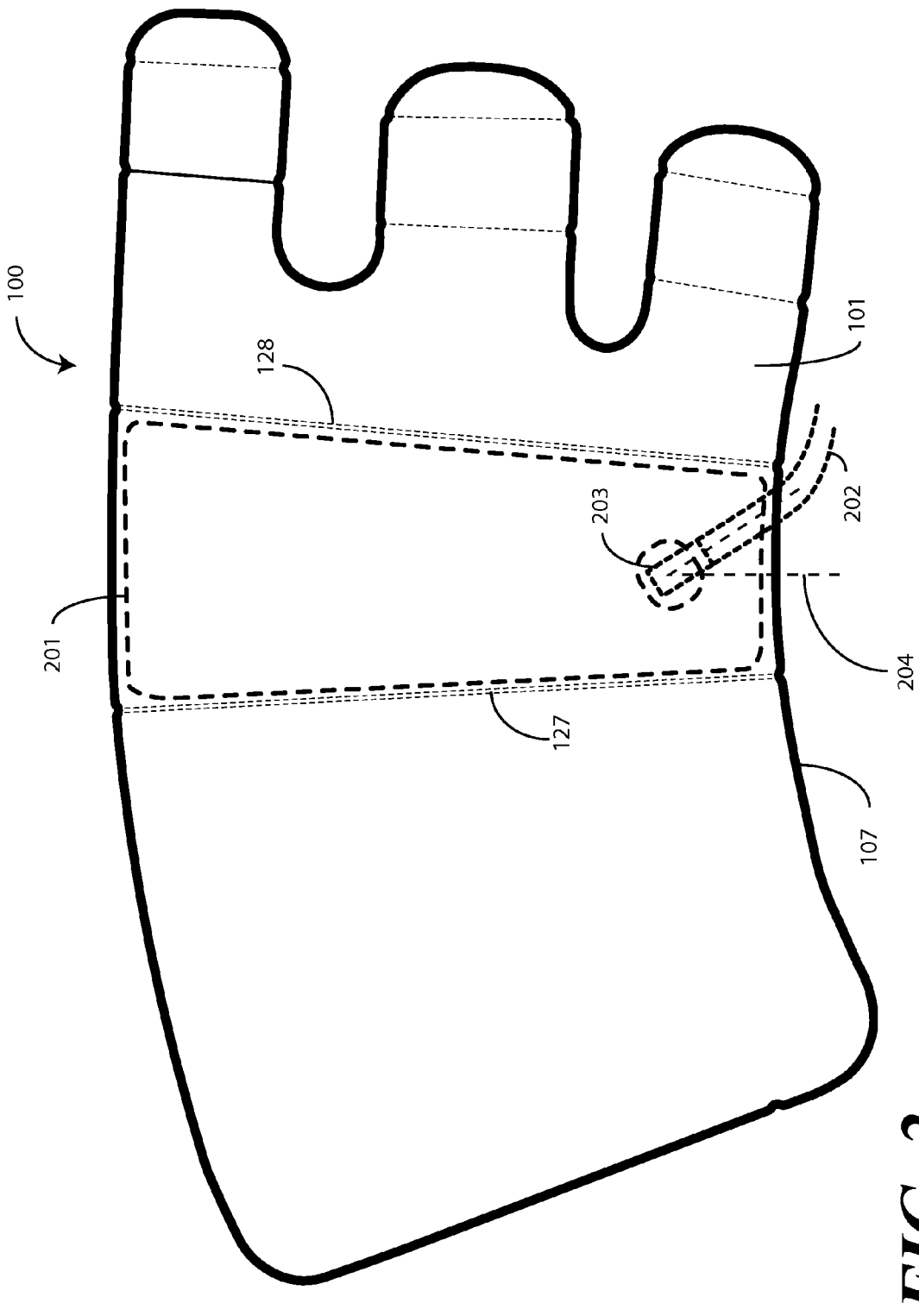
FIG. 2 illustrates a sectional plan view of one explanatory compression device configured for providing compression therapy to a patient limb in accordance with one or more embodiments of the invention.

Turning now to FIG. 2, illustrated therein is a sectional view of the compression device 100. The sectional view is provided to show components of the compression device 100 that are generally not visible when viewing the front side (105). As noted above, in one or more embodiments the wrap 101 can be manufactured from various layers. Accordingly, elements shown in sectional views can be disposed between those layers. Where the wrap 101 is manufactured from a single layer, the components will frequently be disposed on the inner side, and thus will not be visible from the front side (105).

As shown in FIG. 2, in one embodiment the compression device 100 includes a bladder 201 that is configured to be selectively inflatable or deflatable. In one embodiment, the bladder 201 is disposed beneath the central panel (103). In the illustrative embodiment of FIG. 2, this is the case, as the bladder 201 is disposed between stitching 127,128. In one embodiment, the stitching 127,128 defines the bladder 201. In another embodiment, the bladder 201 is a separate component that is held in place by the stitching 127,128. While the central panel (103) is one suitable location for the bladder 201, it is illustrative only. Other locations will be obvious to those of ordinary skill in the art having the benefit of this disclosure. Disposing the bladder 201 along the central panel (103) in a compression device 100 configured for the leg allows the bladder 201 to be positioned beneath the calf muscle of a patient who is lying upon their back.

While the bladder 201 is shown illustratively in FIG. 2 as being a single chamber bladder with no internal welds or chambers, it should be understood that the bladder 201 may also be constructed as a multi-chamber bladder as well. Chambers may be formed with internal weld patterning or other suitable internal patterning including baffling and/or seams provided by welding or other adjoining methods.

In one embodiment, the bladder 201 is inflatable through a connection tube 202. For example, in one application the bladder 201 can be inflated with air to a pressure of forty millimeters of mercury to apply pressure to a patient's limb for compression therapy. The connection tube 202 is coupled to the bladder 201 by way of a connector 203.

In one embodiment, to provide a more comfortable user experience, the connector 203 and connection tube 202 exit the bladder 201 at a non-orthogonal angle 204 relative to the distal edge 107 of the wrap 101. For example, in one embodiment the non-orthogonal angle 204 is about 120 degrees. When the central panel (103) is disposed beneath the patient's leg, for instance, the non-orthogonal angle 204 ensures that the connection tube 202 does not run parallel to the patient's leg, thereby causing discomfort that occurs when the connection tube passes along the patient's Achilles tendon. The non-orthogonal angle 204 causes the connection tube 202 to naturally curve away from the patient's leg, thereby increasing the patient's comfort when using the compression device 100. While 120 degrees is one example of a suitable non-orthogonal angle 204, others will be obvious to those of ordinary skill in the art having the benefit of this disclosure.

Figure 3:
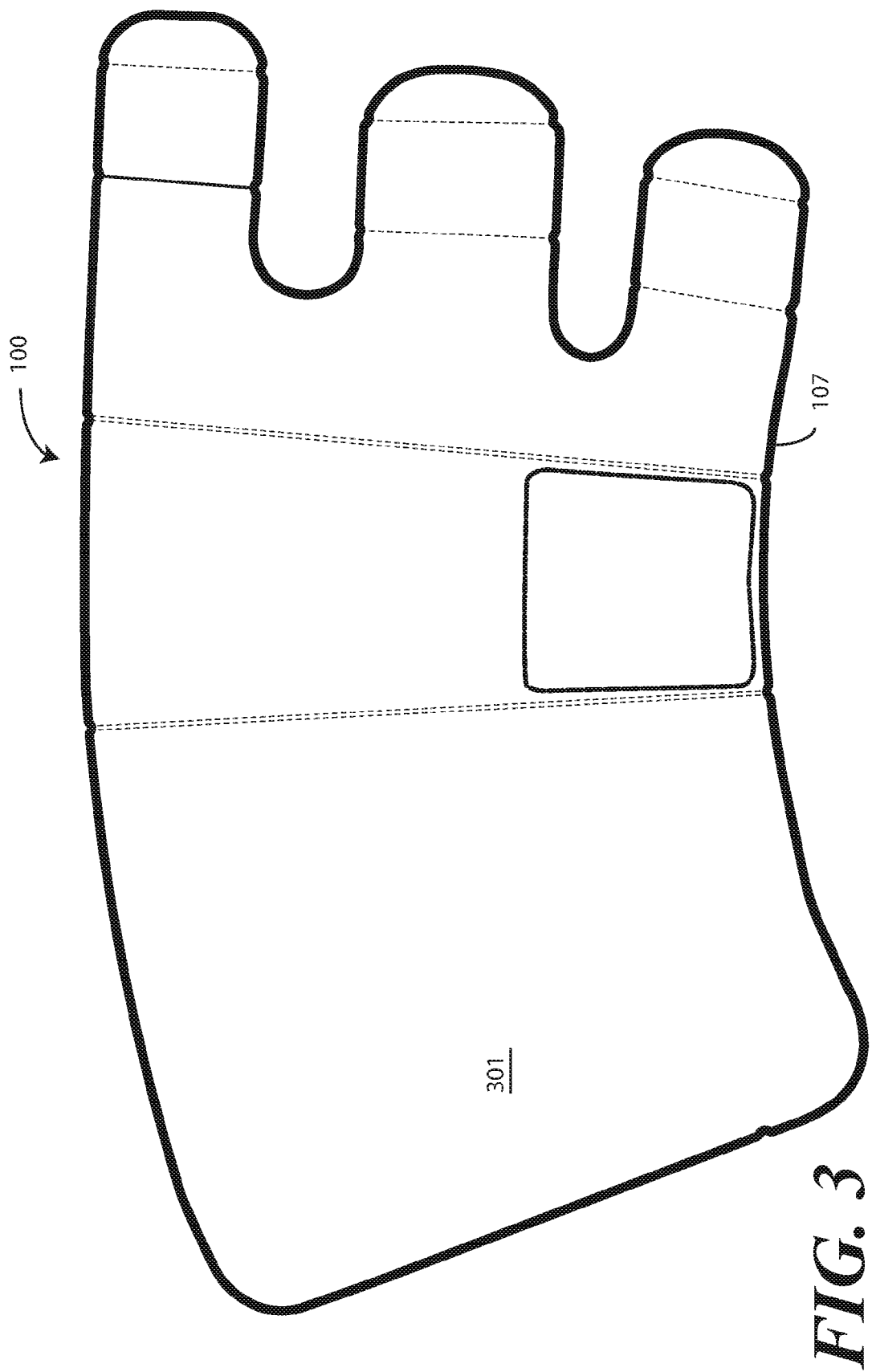
FIG. 3 illustrates another sectional plan view of one explanatory compression device configured for providing compression therapy to a patient limb in accordance with one or more embodiments of the invention.

Turning now to FIG. 3, illustrated therein is another sectional view of the compression device 100. As shown in FIG. 3, one embodiment of the compression device comprises a foam layer 301 disposed adjacent to the distal edge 107 of the wrap 101. In one embodiment, the foam layer 301 extends distally from the distal edge 107 across only a portion of the wrap 101. Comparing FIGS. 2 and 3, it can be seen that in this illustrative embodiment, the foam layer 301 covers the connector (203) of the bladder (201) to slightly elevate the patient's heel when the compression device 100 is in use. This elevation helps to ensure that the connector (203) of the bladder (201) does not become a pressure point against the patient's leg.

Figure 4:
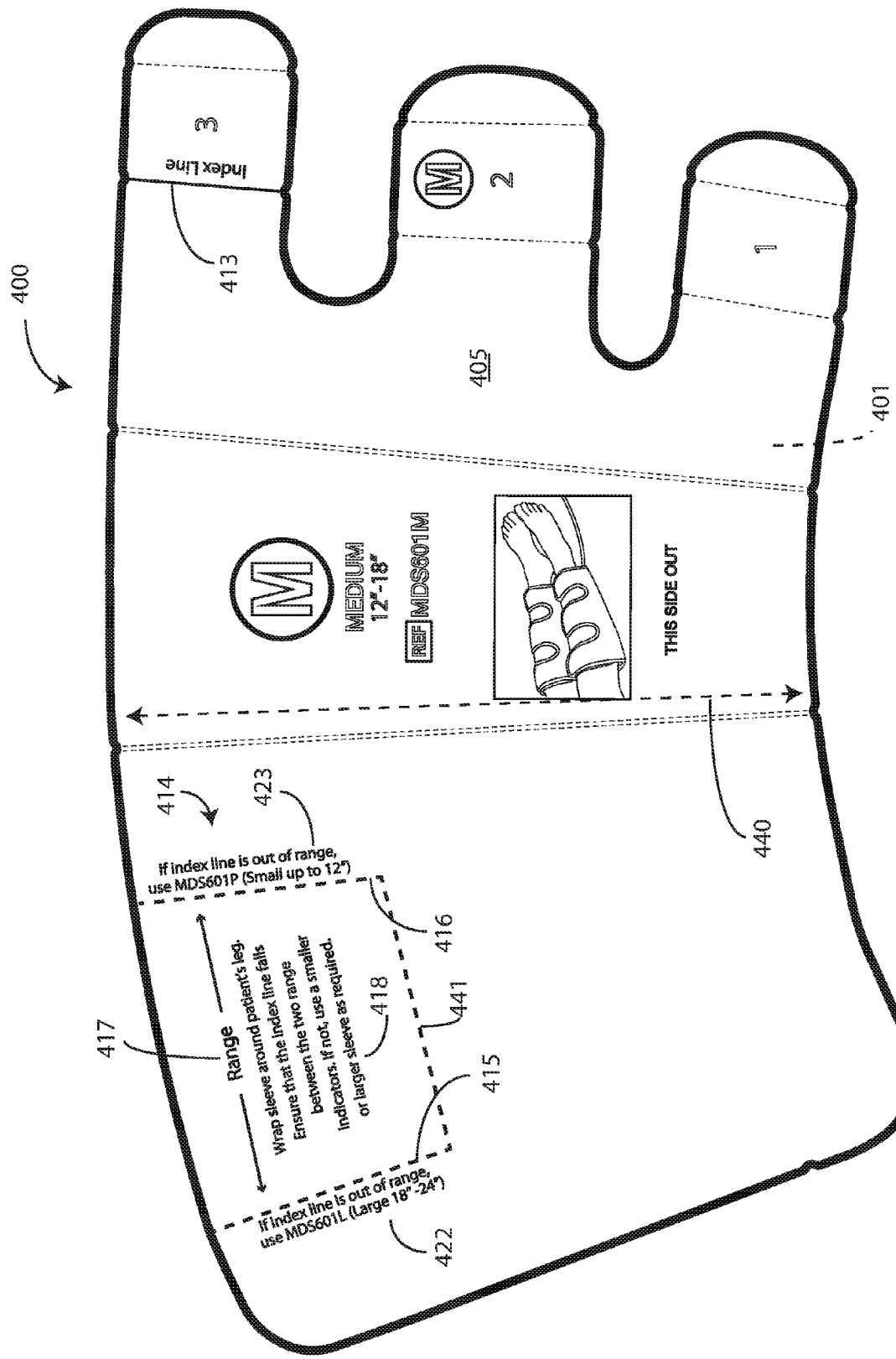
FIG. 4 illustrates a top plan view of another explanatory compression device configured for providing compression therapy to a patient limb in accordance with one or more embodiments of the invention.

Turning now to FIG. 4, illustrated therein is an alternate compression device 400 having a measurement scale 414 that is configured differently from the measurement scale (114) of FIG. 1. As noted above, problems can arise when compression devices are twisted or folded. To help prevent such situations, the longitudinal boundaries 415,416 of FIG. 4 do not traverse the length 440 of the wrap 401. Instead, they traverse only a portion of that length 440, and are intersected by a latitudinal boundary 441. Accordingly, the measurement scale 414 forms not only a longitudinal target for an appropriate fit, but a latitudinal target as well.

In the illustrative embodiment of FIG. 4, the longitudinal boundaries 415,416 begin at the proximal edge 406 and extend distally from the proximal edge 406. They traverse only a portion of the outer face 405, and do not extend to the distal edge 407. In this embodiment, the longitudinal boundaries 415,416 traverse only about a third of the outer face 405. The longitudinal boundaries 415,416 then terminate at the latitudinal boundary 441. The latitudinal boundary 441 can comprise the curvature of the wrap 401, or may alternatively be straight. The latitudinal boundary 441, the longitudinal boundaries 415,416, and the proximal edge 406 thus form a lateral target within which the index line 413 should position for the compression device 400 to provide the appropriate fit when the compression device 400 is wrapped about a patient's limb to provide compression therapy.

This lateral target is an advantage offered by embodiments of the present invention. This advantage is not offered by prior art sizing devices that have been included with devices that wrap about a patient's limb due to the fact that the twisting distortion, which leads to compromised compression therapy, is not known in other fields. Using a blood pressure cuff as an example, lateral alignment is not an issue because the only side affect of improper lateral alignment is a misreading that is easily detectable due to its error. By contrast, in compression therapy, the applicants of the present application have discovered that lateral alignment is of issue in compression therapy because misalignment can result in skin breakdown and/or pressure ulcers. The inclusion of the lateral target offers a distinct advantage that is not provided in prior art sizing devices.

To accommodate shorter longitudinal boundaries 415, 416, in one embodiment the instructions 422,423 can be compressed into double lines to provide an additional mnemonic indicator of the lateral nature of the target. Further, the a range indicator 417 and usage instructions 418 can be moved toward the proximal edge 406 to fit within the measurement scale 414.

Figure 5:
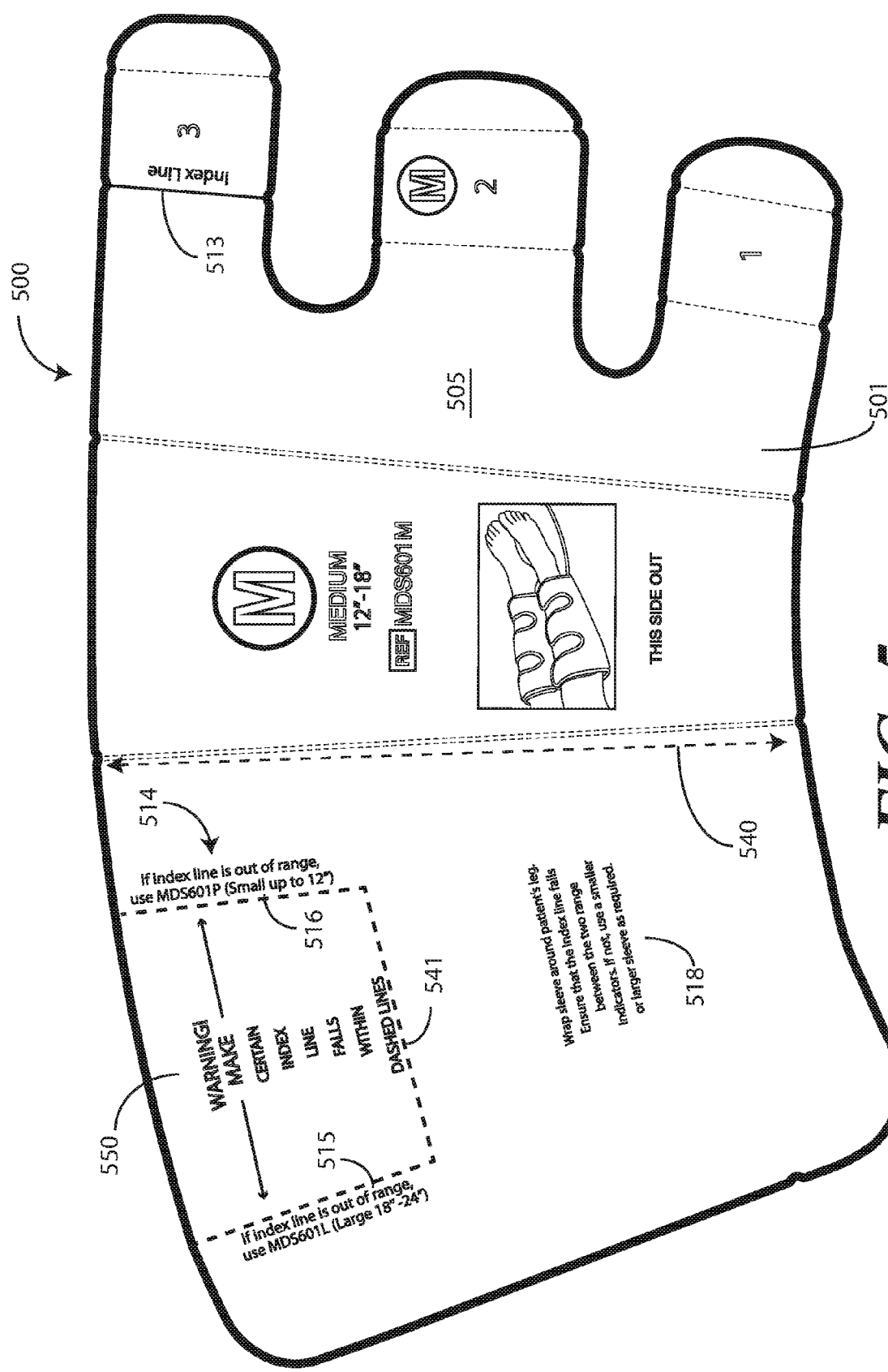
FIG. 5 illustrates a top plan view of another explanatory compression device configured for providing compression therapy to a patient limb in accordance with one or more embodiments of the invention.

Turning now to FIG. 5, illustrated therein is another alternate compression device 500 having a measurement scale 514 that is a variation of the measurement scale (414) of FIG. 4. As with FIG. 4, the measurement scale 514 of FIG. 5 has longitudinal boundaries 515,516 that do not traverse the length 540 of the wrap 501. Instead, they traverse only a portion of that length 540, and are intersected by a latitudinal boundary 541. Accordingly, the measurement scale 514 forms not only a longitudinal target for an appropriate fit, but a latitudinal target as well.

However, rather than having the usage instructions 518 disposed within the lateral target formed by the proximal edge 506, the longitudinal boundaries 515,516 and the latitudinal boundary 541, the usage instructions 518 have been moved outside of the lateral target. This allows either no information or other information 550 to be disposed within the lateral boundary.

For example, in some applications the lateral boundary will provide more of a mnemonic reminder that the index line 513 should fall therein when it is blank. Accordingly, moving the usage instructions 518 outside the lateral target provides for this. In other applications, making the lateral target a different color from the outer face 505 of the wrap 101 will provide a more effective mnemonic reminder. Again, moving the usage instructions 518 outside of this area facilitates such coloring.

In the illustrative embodiment of FIG. 5, other information 550 emphasizing that the index line 513 should fall within the lateral target is included. Specifically, in this embodiment the other information 550 states, "Warning! Make certain index line falls within dashed lines." This provides a clear indication to the health care services provider that the lateral target not only serves a decorative purpose, but provides a utilitarian function as well. Other messages suitable for use as the other information 550 will be obvious to those of ordinary skill in the art having the benefit of this disclosure. The embodiment of FIG. 5 is illustrative of some of the many variations in which embodiments of the invention can be configured.

Figure 6:
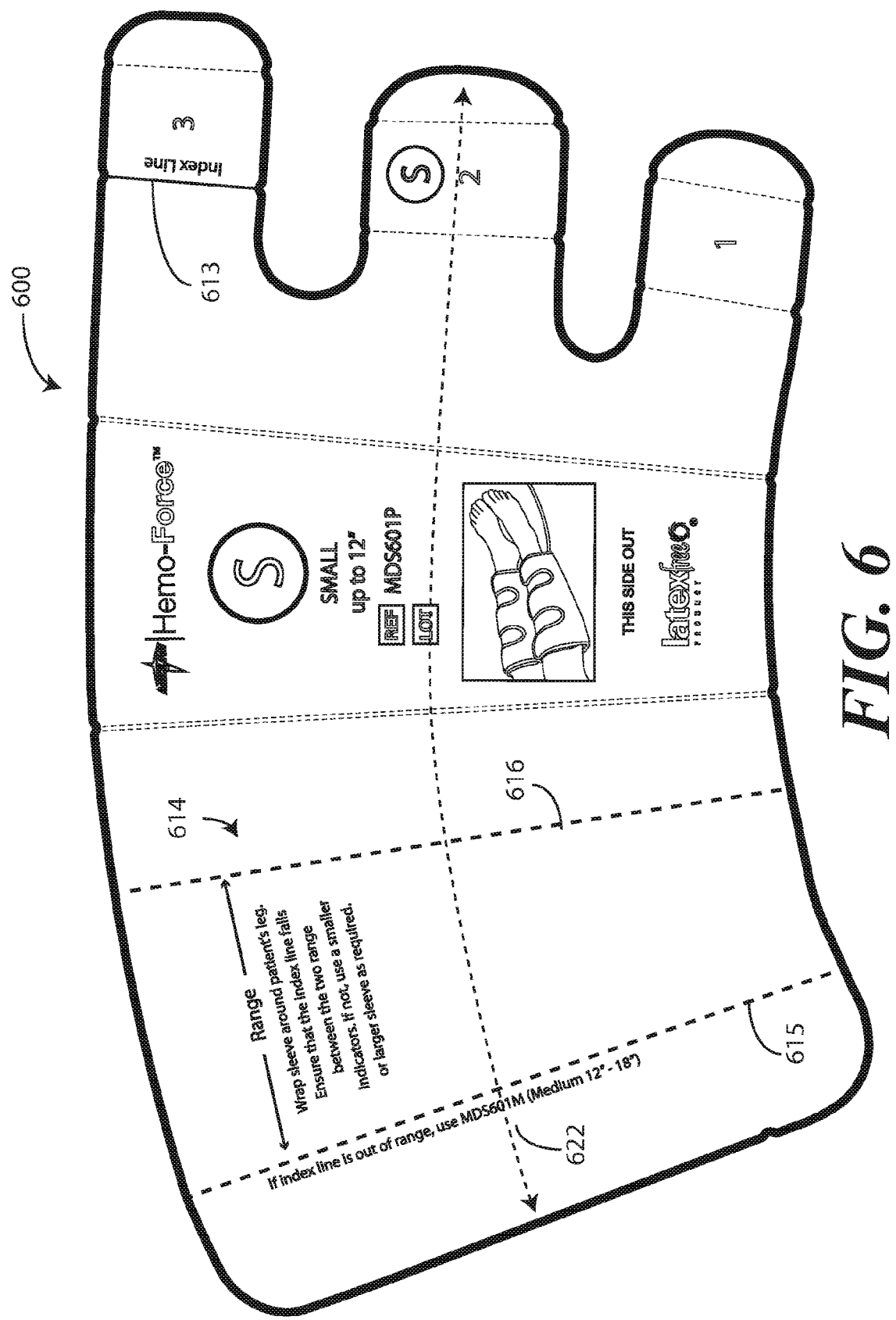
FIG. 6 illustrates a top plan view of another explanatory compression device configured for providing compression therapy to a patient limb in accordance with one or more embodiments of the invention.

Turning now to FIG. 6, illustrated therein is yet another compression device 600 configured in accordance with embodiments of the invention. Recall from above that the compression device (100) of FIG. 1 was a medium-sized compression device. The embodiment of FIG. 6 is a small. Changes in size will result, in some embodiments, in the measurement scale 414 being modified.

As with FIG. 1, the compression device 600 of FIG. 6 has a measurement scale 614 disposed thereon, with the measurement scale 614 having two longitudinal boundaries 615,616 identifying a range within which the index line 613 should position for the compression device 600 to provide an appropriate fit for providing compression therapy. However, in FIG. 6, the longitudinal boundaries 615,616 are configured for a "small" sized compression device 600. Accordingly, there may be no smaller size. Thus, while instructions 622 directing a health care services provider with specifics as to what action to take next if the index line 613 falls to the left of longitudinal boundary 615, no instructions are provided adjacent to longitudinal boundary 616. If the compression device 600 were an extra-large device, the opposite may be true. To wit, instructions may be placed adjacent to the rightmost longitudinal boundary, with none being provided by the leftmost longitudinal boundary.

Figure 7:
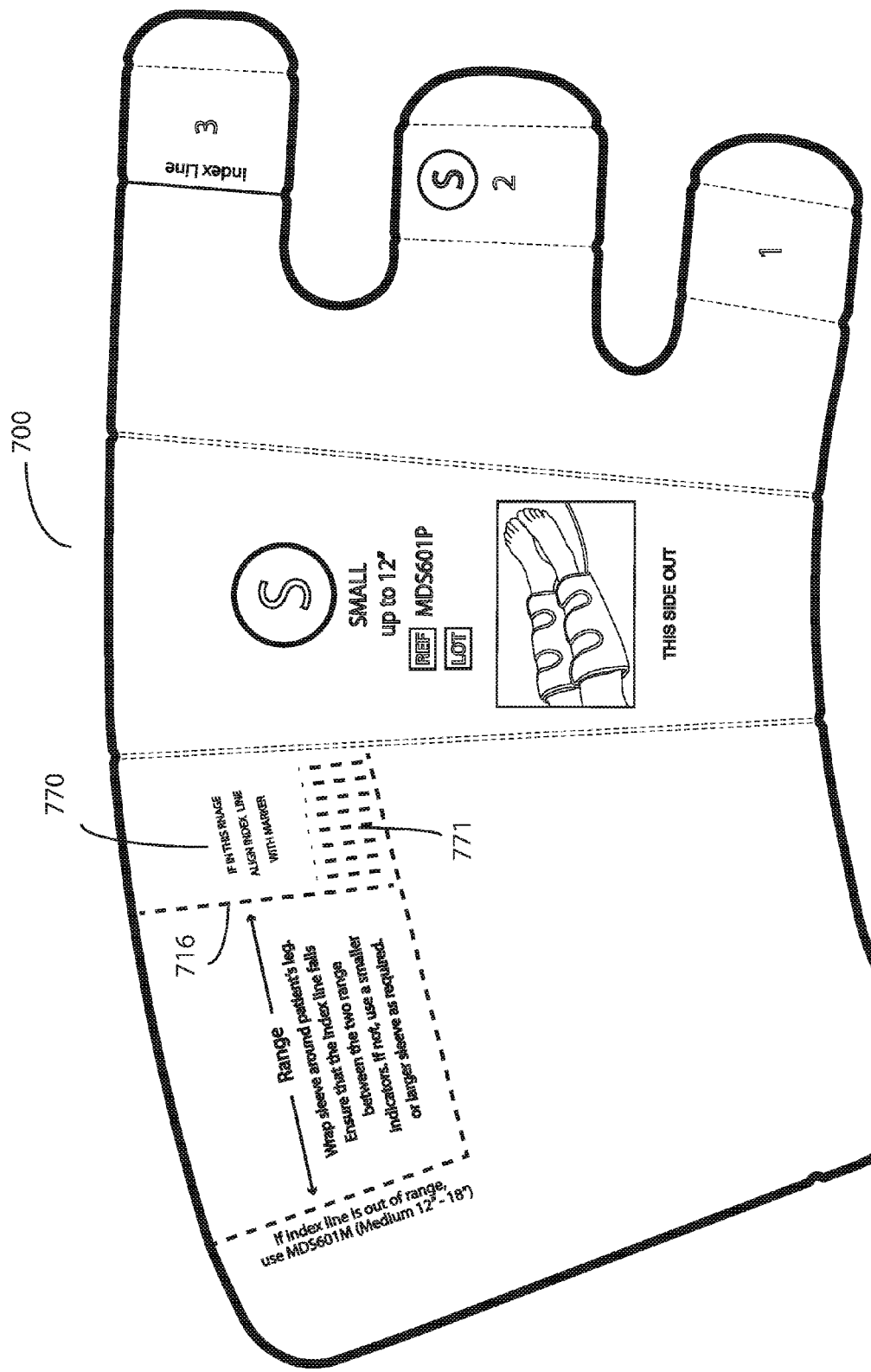
FIG. 7 illustrates a top plan view of explanatory compression device configured for providing compression therapy to a patient limb in accordance with one or more embodiments of the invention.

As with the variations of the measurement scale described in FIGS. 1, 4, and 5, the embodiment of FIG. 6, i.e., where there is no next size on one side of the equation, can be varied as well. Turning now to FIG. 7, illustrated therein is a compression device 700 having one such variation. As shown, rather than including instructions adjacent to the "out of range" longitudinal boundary 716, out of range instructions 770 are provided. In this illustrative embodiment, the out of range instructions include a plurality of index line alignment markers 771 and the instruction "If in this range, align index line with marker." Such an instruction help avoid the twisting problem described above. Other out of range instructions will be obvious to those of ordinary skill in the art having the benefit of this disclosure. The embodiment of FIG. 7 is illustrative only of the flexibility in variation offered by embodiments of the present invention.

Figure 8:
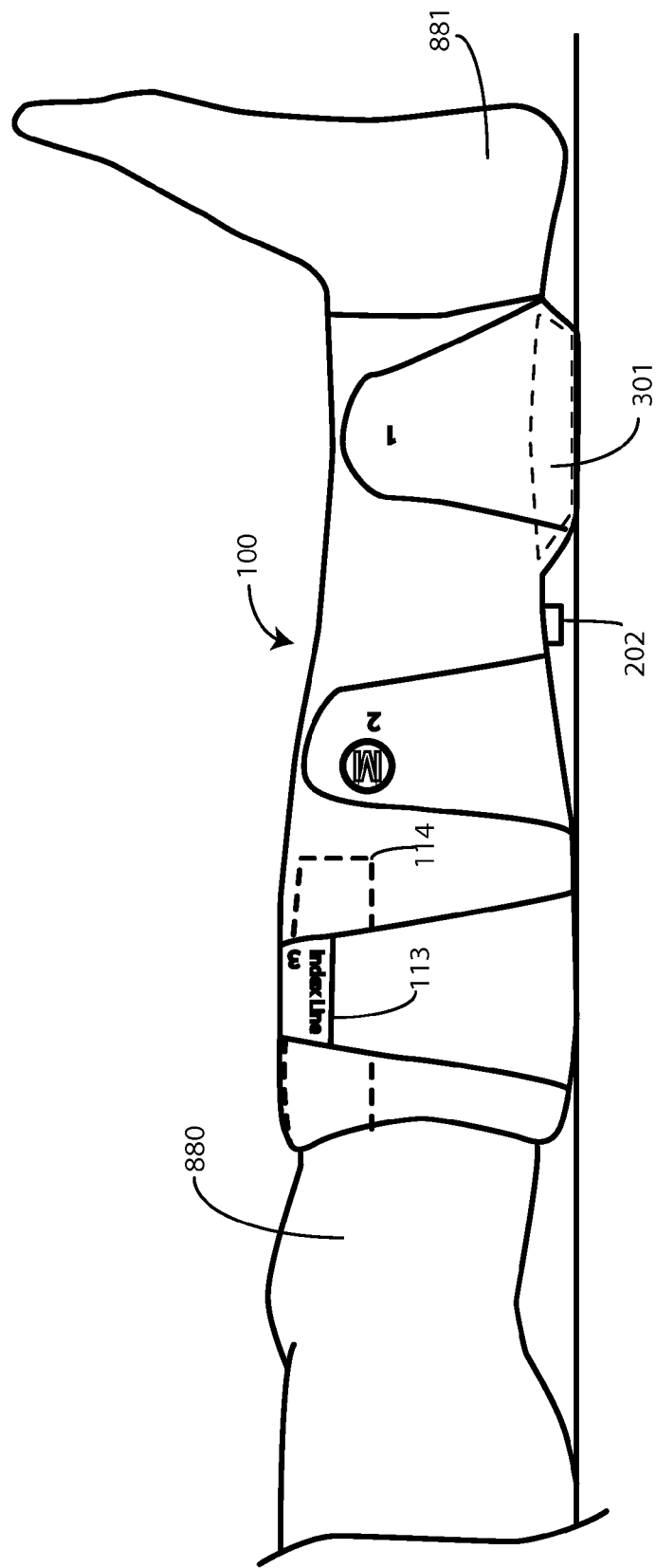
FIG. 8 illustrates a patient wearing one explanatory compression device configured for providing compression therapy to a patient limb in accordance with one or more embodiments of the invention.

Turning now to FIG. 8, illustrated therein is a side elevation view of one embodiment of a compression device 100 wrapped about a patient's leg 880. As shown, this embodiment includes the foam layer 301 that is configured to lift the patient's heel 881. This allows the connection tube 202 to extend at its non-orthogonal angle (204) from the bladder (201), which has been inflated, without applying pressure to the patient's leg or Achilles tendon. Further, the inclusion of the foam layer 301 can work to prevent possible abrasions, shearing, or application of unnecessary pressure that may affect the patient's circulation. As shown, the compression device 100 properly fits the patient, as the index line 113 positions within the measurement gauge when the compression device 100 is wrapped about the patient's leg 880.

Figure 9:
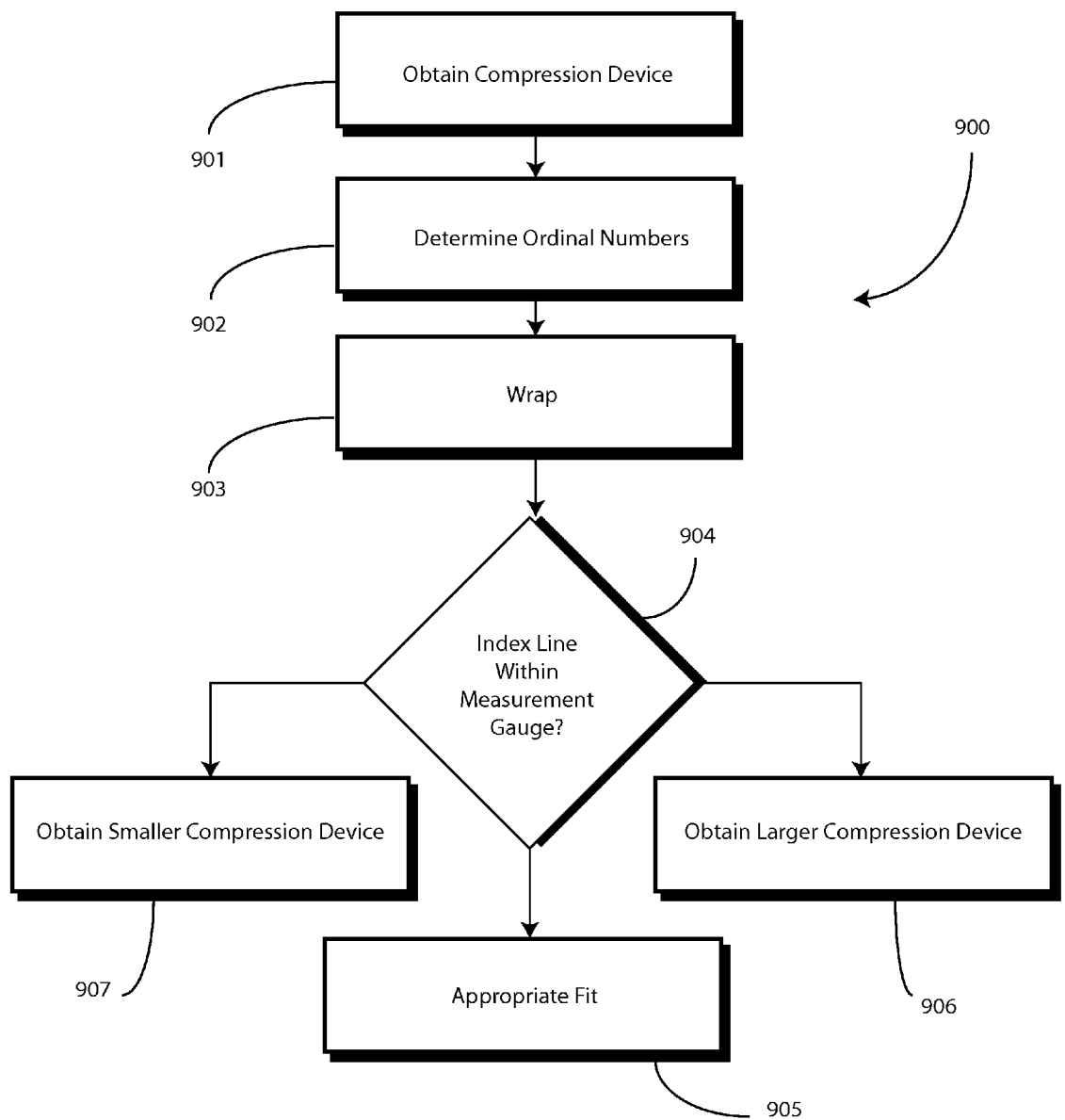
FIG. 9 illustrates a method of using one explanatory compression device configured for providing compression therapy to a patient limb in accordance with one or more embodiments of the invention.

Turning now to FIG. 9, illustrated therein is one explanatory method 900 of applying a compression device to a patient limb to provide compression therapy in accordance with one or more embodiments of the invention. At step 901, a health care services provider first obtains a compression device. In one embodiment, the compression device includes a wrap comprising an outer face defining a proximal edge, a distal edge, a first side edge, and a second side edge. The second side edge can comprise or define a plurality of attachment tabs, with an index line disposed on at least one of the plurality of attachment tabs. The compression device can include a measurement scale disposed along the outer face comprising longitudinal boundaries identifying a range within which the index line should position for the compression device to provide an appropriate fit for the providing of the compression therapy when the compression device is wrapped about the patient limb. The compression device can be color coded, with the color corresponding to a particular size of the compression device. Accordingly, step 901 can include determining the proper size of compression device to obtain. This can include identifying the proper size by color.

The compression device can include ordinal numbers indicative of a predefined order in which the attachment tabs should be wrapped about the patient's leg. Where this is the case, optional step 902 can be included in the method 900. At step 902, the method 900 can include determining ordinal numbers disposed along a plurality of attachment tabs extending from a side of the compression device.

At step 903, the method 900 includes wrapping the compression device about a patient's limb. Where the ordinal numbers are included along the attachment tabs, step 903 can include attaching each of the plurality of attachment tabs in an order corresponding to the ordinal numbers. This step 903 can also include attaching an attachment tab of the compression device to an outer face of the compression device.

At decision 904, the method 900 determines whether the index line disposed on an attachment tab is within a measurement scale disposed on the outer face of the compression device. Where it is, as indicated at step 905, an appropriate fit has been achieved. If a bladder is disposed within the compression device, it can now be inflated.

However, when the index line positions between a longitudinal boundary of the measurement scale and a first side edge of the compression device, as indicated at step 906, the method 900 includes obtaining a larger compression device. In one embodiment, this step 906 includes reading instructions of the measurement scale to determine what part number to retrieve. When the index line positions between another longitudinal boundary of the measurement scale and a second side edge of the compression device, as indicated at step 907, the method 900 can include obtaining a smaller compression device. In one embodiment, this can include reading instructions of the measurement scale to determine what part number to retrieve.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A compression device configured for providing compression therapy to a patient limb, the compression device comprising:
   a wrap comprising an outer face defining a proximal edge, a distal edge, a first side edge, and a second side edge, wherein the second side edge defines a plurality of attachment tabs;
   an index line disposed on at least one of the plurality of attachment tabs; and
   a measurement scale disposed along the outer face comprising longitudinal boundaries identifying a range within which the index line should position for the compression device to provide an appropriate fit for the providing of the compression therapy when the compression device is wrapped about the patient limb;
   wherein the wrap defines a medial reference line having a curvature configured to facilitate the wrap wrapping about the patient limb, wherein the longitudinal boundaries are oblique relative to each other so as to both be orthogonal with the medial reference line.

2. The compression device of claim 1, wherein the longitudinal boundaries define a quasi-frustoconical shape.

3. The compression device of claim 1, wherein the longitudinal boundaries extend distally from the proximal edge and traverse only a portion of the outer face.

4. The compression device of claim 3, wherein the longitudinal boundaries traverse about a third of the outer face.

5. The compression device of claim 3, wherein the longitudinal boundaries terminate at a latitudinal boundary comprising the curvature, thereby defining a lateral target within which the index line should position for the compression device to provide the appropriate fit for the providing of the compression therapy when the compression device is wrapped about the patient limb.

6. The compression device of claim 1, wherein the index line is disposed only on an attachment tab adjacent to the proximal edge.

7. The compression device of claim 6, wherein the plurality of attachment tabs each have an ordinal number disposed thereon indicating in which order the plurality of attachment tabs are to be attached to the outer face of the wrap.

8. The compression device of claim 7, wherein a greatest ordinal number is disposed on the attachment tab adjacent to the proximal edge.

9. The compression device of claim 1, wherein:
   the wrap comprises a central panel having indicia identifying a size of the compression device disposed thereon; and
   the at least one of the plurality of attachment tabs has corresponding indicia identifying the size of the compression device disposed thereon.

10. The compression device of claim 9, wherein the index line and the corresponding indicia identifying the size of the compression device are disposed on different attachment tabs.

11. The compression device of claim 9, wherein the outer face is color-coded with a color visually indicative of the size.

12. The compression device of claim 9, wherein:
   a perimeter of the wrap is color-coded with a color, different from another color of the wrap; and
   a combination of the color and the another color are configured to be visually indicative of the size.

13. The compression device of claim 1, wherein the wrap comprises a central panel comprising an inflatable bladder configured to be selectively inflatable through a connection tube to apply pressure to the patient limb, wherein the connection tube exits the inflatable bladder at a non-orthogonal angle relative to the distal edge.

14. The compression device of claim 13, wherein the central panel further comprises a foam layer extending distally from the distal edge across only a portion of the central panel.

15. The compression device of claim 1, wherein the measurement scale comprises instructions, disposed between one of the longitudinal boundaries and the first side edge, indicating that a larger compression device is required when the index line positions between the one of the longitudinal boundaries and the first side edge when the compression device is wrapped about the patient limb.

16. The compression device of claim 15, wherein the measurement scale comprises additional instructions, disposed between another of the longitudinal boundaries and the second side edge, indicating that a smaller compression device is required when the index line positions between the another of the longitudinal boundaries and the second side edge.

17. A method of applying a compression device to a patient limb to provide compression therapy, comprising:
wrapping the compression device about the patient limb;
attaching an attachment tab of the compression device to an outer face of the compression device; and
determining whether an index line disposed on the attachment tab is within a measurement scale disposed on the outer face of the compression device, the measurement scale comprising a first longitudinal boundary that is oblique relative to a second longitudinal boundary, where both the first longitudinal boundary and the second longitudinal boundary are orthogonal to a medial reference line of the compression device.

18. The method of claim 17, wherein when the index line positions between a longitudinal boundary of the measurement scale and a first side edge of the compression device, obtaining a larger compression device.

19. The method of claim 18, wherein when the index line positions between another longitudinal boundary of the measurement scale and a second side edge of the compression device, obtaining a smaller compression device.

20. The method of claim 17, further comprising:
determining ordinal numbers disposed along a plurality of attachment tabs extending from a side of the compression device; and
attaching each of the plurality of attachment tabs in an order corresponding to the ordinal numbers.

* * * * *